United States Patent [19]

Yang

[11] Patent Number: 4,483,773

[45] Date of Patent: Nov. 20, 1984

[54] NARROW BORE MICRO-PARTICULATE COLUMN PACKING PROCESS AND PRODUCT

[75] Inventor: Frank J. Yang, Danville, Calif.

[73] Assignee: Varian Associates, Inc., Palo Alto, Calif.

[21] Appl. No.: 604,412

[22] Filed: Apr. 30, 1984

Related U.S. Application Data

[63] Continuation of Ser. No. 432,470, Oct. 4, 1982, abandoned.

[51] Int. Cl.³ .......................................... B01D 15/08
[52] U.S. Cl. ..................................... 210/656; 55/67; 55/386; 210/198.2
[58] Field of Search .................... 210/656, 659, 198.2; 55/67, 386

[56] References Cited

U.S. PATENT DOCUMENTS 4,102,782  7/1978  Saito et al. ..................... 210/198.2
4,293,415 10/1981  Bentz et al. ..................... 210/198.2

OTHER PUBLICATIONS

High Performance Liquid Chromatography by Knox, Edinburg University Press, Edinburg, Scotland, pp. 147-153, relied on, 1978.
Column Packing System for High Performance Liquid Chromatography, by Grover et al., Lab. Practices, vol. 31, No. 2, (Feb. 1982), pp. 110-112, relied on.

Primary Examiner—John Adee
Attorney, Agent, or Firm—Stanley Z. Cole; Keiichi Nishimura; Norman E. Reitz

[57] ABSTRACT

A process for packing narrow bore chromatographic columns and the resulting product are provided. A flexible column, preferably of fused silica, of inner diameter less than 500 $\mu m$ is selected. A slurry is formed in a reservoir from a mobile solvent and particles of specified diameter. For liquid chromatography the particle size ranges from 3 $\mu m$ to 10 $\mu m$; for gas chromatography the particle size ranges from 3 $\mu m$ to 100 $\mu m$. An end restriction is placed in the end of the column to permit the flow of mobile solvent and to restrict the passage of particles out the end of the column. The reservoir is attached to the column and the slurry is caused to flow under pressure into the column. A two-step pressure sequence is used to first set up the bed of particles and then to compress the bed. First, an initial pressure is maintained for an initial period, preferably less than 10 minutes. Next, the pressure is raised from the initial pressure to a maximum pressure and is maintained at the maximum pressure for a second period. The product in either case is a stable, loose packed column having a high plate number per unit length.

17 Claims, 15 Drawing Figures

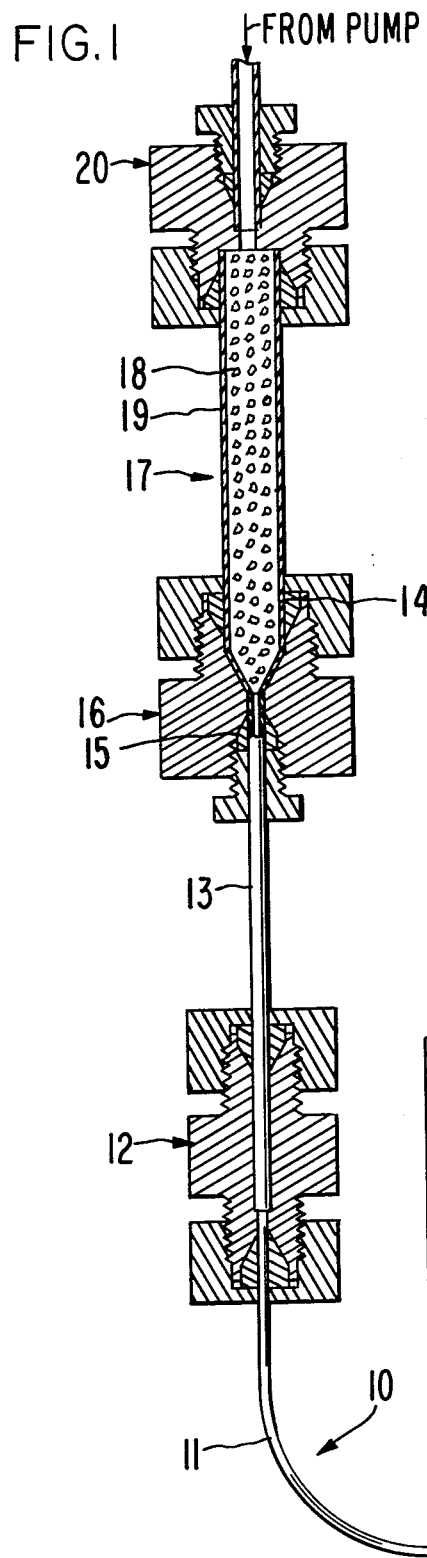
FIG. 1
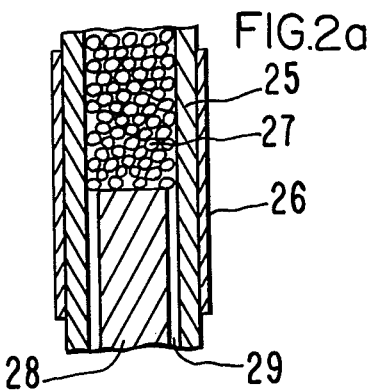
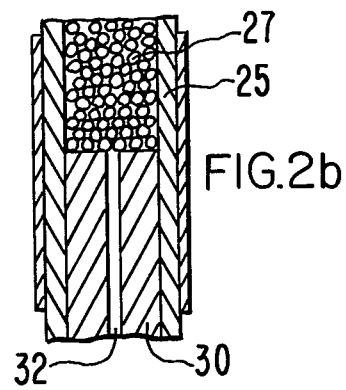
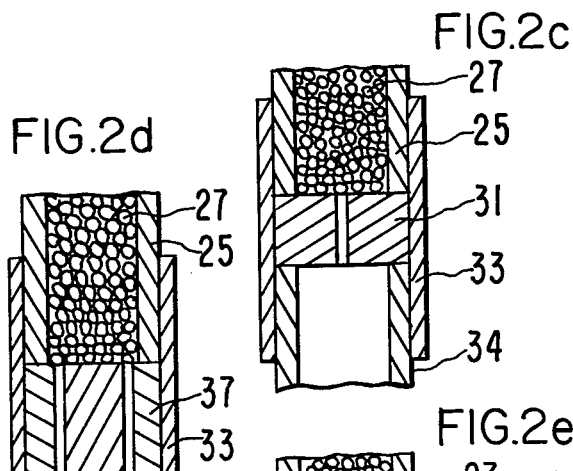
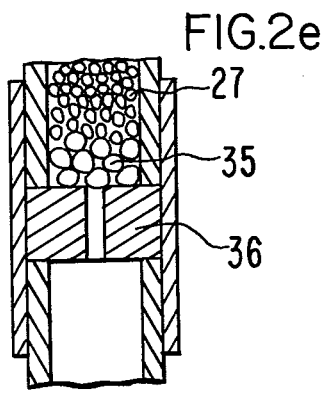

FUSED-SILICA COLUMN PACKED WITH 3 μm PARTICLES, 1m x 0.3 mm ID SEM VIEWED AT THE COLUMN INLET END NEAR THE CENTER OF THE COLUMN CROSS-SECTION $2.4 \cdot 10^3$ X CROSS SECTIONAL VIEW OF A FUSED-SILICA COLUMN PACKED WITH 3 μm PARTICLES, 1m x 0.3 mm ID $2.6 \cdot 10^2$ X FUSED-SILICA COLUMN PACKED
WITH 3 μm PARTICLES,
1m x 0.3 mm ID
SEM VIEWED AT THE COLUMN
OUTLET END NEAR THE WALL
1.7 · 10³ X FUSED-SILICA COLUMN PACKED
WITH 3 μm PARTICLES,
1m x 0.3 mm ID
SEM VIEWED AT THE COLUMN
INLET END NEAR THE WALL
2.4 · 10³ X

**FUSED-SILICA COLUMN PACKED
WITH 3 μm PARTICLES,
1m x 0.3 mm ID
SEM VIEWED AT THE COLUMN
OUTLET END NEAR THE WALL
$2.4 \cdot 10^3$ X**

NARROW BORE MICRO-PARTICULATE COLUMN PACKING PROCESS AND PRODUCT

This application is a continuation, of U.S. application Ser. No. 432,470, filed 10/04/82 abandoned.

This invention relates to a process for packing chromatographic columns and the resulting product and more particularly relates to a process for packing a narrow bore microparticle packed chromatographic column for use in gas or liquid chromatography and the resultant product.

The trend in chromatography has been to move to higher pressures and smaller diameter columns for efficient solvent utilization in high performance liquid chromatography (HPLC) and for high column efficiency in gas chromatography (GC). In addition, the desire to obtain greater resolving power can be realized by using long columns. As a result of these developments complex mixtures may be effectively separated while using smaller amounts of mobile solvent in LC and minimum analysis time in GC. For a discussion of these developments see F. J. Yang, "Fused-Silica Narrow-Bore Microparticle-Packed-Column High-Performance Liquid Chromatography", *Journal of Chromatography*, v. 236, p. 265 (1982). The results of these developments is that new chromatographic apparatus and more powerful chromatographic techniques are being provided.

Whereas in gas chromatography the highest resolution and speed of analysis has been obtained by using narrow bore open tubular columns (see, e.g., P. F. Bente, III, et al., "Silica Chromatographic Column", U.S. Pat. No. 4,293,415), in liquid chromatography the highest resolution has been obtained primarily with narrow bore microparticle packed columns. This latter circumstance for liquid chromatography is due to the fact that small particles (e.g., $\leq 10$ $\mu$m) can be packed efficiently in long lengths of narrow bore columns. For a discussion of developments in HPLC as contrasted to developments in gas chromatography see, for example, F. J. Yang, "Narrow-Bore Microparticle-Packed Column High-Performance Liquid Chromatography", J. Chromatography, Proceedings, The VI International Liquid Column Chromatography Conference (1982).

Since narrow bore microparticle packed columns offer advantages in performance for HPLC and even for GC, it is therefore required that satisfactory column and packing materials and techniques be developed to pack such columns. Older, gravitational methods of packing columns have not proven satisfactory for narrow bore columns. See G. H. Lathe, et al., "Separation of Substance and Estimation of Their Relative Molecular Sizes by the Use of Columns of Starch in Water", Biochemical Journal, v. 62, p. 665 (1950) and P. Flodin, "Methodological Aspects of Gel Filtration with Special Reference to Desalting Operations", Journal of Chromatography v. 5, No. 2, p. 103 (1961). One technique for packing narrow diameter columns is to pack a conventional glass column and then heat and draw the column to a narrower diameter. LC stationary phases have then been bonded in situ. See M. Novotny, et al., "Packed Microcapillary Columns in High Performance Liquid Chromatography", Anal. Chem., 50 271 (1978). The products formed by this technique are different from conventional packed columns in that the columns have low ratios of column diameter to particle size, in the range of about 2-3. The disadvantage with this approach is that due to the relatively large particle sizes used, the performances of the packed microcapillary columns is markedly inferior to columns of conventional diameter of 4 to 5 mm which are packed with 5 $\mu$m particles. Particle sizes smaller than 30 $\mu$m cannot be packed by using this technique due to clogging and the difficulty in obtaining uniform packing. As may be appreciated, it generally becomes difficult to pack progressively narrower columns with microparticles since the inner diameter of the columns begins to approach the particle size so that non-uniform packing and clogging of the columns may occur or the product may have high resistances to flow of solvent. And as column lengths are increased, the problem is exacerbated.

Other column packing techniques used for packing 4 to 5 mm ID LC columns are also known. These include the balanced slurry packing developed by R. E. Majors, Anal. Chem. 44 1722, 1723 (1972) and J. J. Kirkland, J. Chromatogr. Sci., 9 206, 207 (1971) for LC packed columns; and conventional high pressure air compression dry bed packing employed with GC columns. For small diameter columns, e.g., columns having inner diameters of 500 microns or less, it is known to incorporate the particles in a slurry and flow the slurry through the column. For example, see the brochure, "LC Slurry Packing Kit", Scientific Systems, Inc., State College, PA 16801. The slurry packing technique is typically practiced by achieving a flow of the slurry through the column, stopping the flow, draining off the liquid and retaining the particles then present in the column. Studies of this technique have evaluated the relationship between packing velocity and column size, see Y. Kato, et al., "Packing of Toyopearl Column For Gel Filtration", J. Chromatography, v. 205, p. 185 (1981), v. 206, p. 135 (1981), and have shown that semi-constant pressure packing with variable flow velocity may be preferred for packing columns for gel filtration (see Y. Kato, et al., "Packing of Toyopearl Columns For Gel Filtration, 111, Semi-Constant Pressure Packing", J. Chromatography, v. 208, p. 71 (1981).

In D. Ishii, et al., "Development of Technique for Miniaturization of High-Performance Liquid Chromatography", *J. Chromatography*, v. 144, p. 157, 1977, a column made of PTFE tubing of 0.5 mm I.D. and 1.0 mm O.D. was prepared by a slurry packing technique. A tube several times longer than required for the finished column was selected. The stationary phase was suspended in a suitable solvent as a slurry, which was placed in a small bottle. A 250 microliter airtight syringe was connected with the tube and they were filled with the solvent that was used to prepare the slurry. The lower end of the tube was then dipped into the slurry, the syringe was attached to a microfeeder and the slurry was sucked up to the upper end of the tube by either manual or electrical operation of the feeder. The lower end of the tube was then plugged tightly with a small amount of quartz wool to stop the packing material from leaking out. The microfeeder was operated manually or electrically to discharge the solvent. The resultant columns have a poor packed bed stability and are easily deformed at high flow rates and high column inlet pressures. They are not suitable for high pressure liquid chromatography (HPLC).

It is therefore an object of the present invention to provide a process for packing narrow bore high efficiency columns selected from the materials of fused-silica, glass, stainless steel, or glass-lined stainless steel.

It is another object of the present invention to provide a process for uniformly packing a narrow-bore chromatographic column over its length with microparticles having a diameter in the range of 3 μm to 10 μm for liquid chromatography and 3 μm to 100 μm for gas chromatography.

It is a further object of the present invention to provide a narrow-bore microparticle packed chromatographic column of uniformly low porosity and stable packed bed.

It is another object of the present invention to provide a column having ends for connection to the injector and detector interface which achieves optimum column efficiency and packed bed stability.

BRIEF DESCRIPTION OF THE DRAWING

For a more complete understanding of the present invention reference may be had to the accompanying drawings which are incorporated herein by reference and in which:

FIG. 1 is a cross-sectional view of a fixture for packing a narrow-bore chromatographic column in accordance with the process of the present invention;

FIGS. 2a-2e are side cross-sectional views of alternative end fittings for use in the end of a narrow-bore chromatographic column when it is being packed in accordance with the process of the present invention;

SUMMARY OF THE INVENTION

Figure 3:
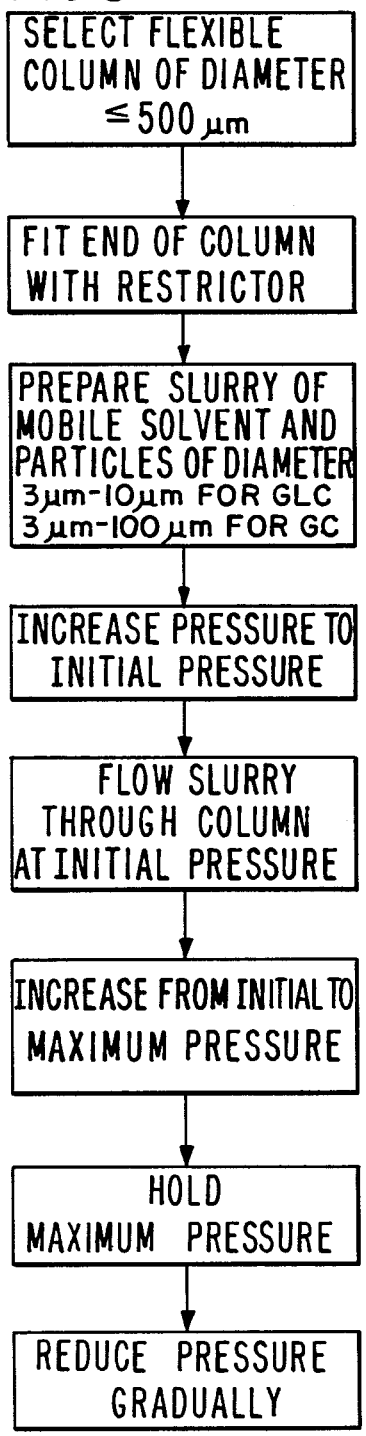
FIG. 3 is a process flowchart describing the column packing process of the present invention.

A process for packing narrow bore chromatographic columns is provided. A flexible column of inner diameter less than 500 μm is selected. A slurry is formed in a reservoir from a mobile solvent and particles of specified diameter. For liquid chromatography the particle size ranges from 3 μm to 10 μm; for gas chromatography the particle size ranges from 3 μm to 100 μm. An end restriction is placed on the end of the column to permit the flow of mobile solvent and to restrict the passage of particles out the end of the column. The reservoir is attached to the column and the slurry is caused to flow under pressure into the column. A two-step pressure sequence is used to first fill up and form the bed of particles and then to uniformly compress the bed. Thus, an initial pressure is maintained for an initial period of time, preferably less than 10 minutes. Next, the pressure is raised from the initial pressure to a maximum pressure for a second period. The product is a stable, yet loose packed column having a high plate number per unit length.

DESCRIPTION OF THE PREFERRED EMBODIMENTS

The ultimate aim in packing columns is to obtain reproducibly uniform distributions of the packing materials both across and along the length of the columns. Such uniformly packed columns will tend to have high resolving power and be susceptible to being used for high speed analysis. As discussed previously, gravitational, dry packing and slurry packing techniques have been employed. As column diameters have become narrower, e.g., ≦500 μm, they become increasingly more difficult to pack in a reproducible manner. Poor uniformity has resulted due to wall effects when conventional slurry packing techniques have been used. Microparticles smaller than 5 μm have been particularly difficult to pack and non-uniform packing density as well as low porosity has resulted.

As seen in Table I, in the development of narrow bore microparticle packed columns for HPLC, certain column categories have emerged.

TABLE I

| Designation | Column ID (μm) | Particle Size (μm) | Flow Rate (μl/min) |
| --- | --- | --- | --- |
| Unpacked Microcapillary | ≦50 | — | <<0.01 |
| Packed Microcapillary | 50–200 | 10–100 | <0.1 |
| Packed Small-Bore | 500–1000 | 5–20 | 20–100 |
| Packed Narrow-Bore | 50–500 | 3–10 LC 3–100 GC | 0.1–20 |

Each category has its own range of column I.D., particle size and flow rate. While potentially difficult to fabricate, the microcapillary columns require only small amounts of packing material and are economical to operate since they only use small amounts of solvent. In packing narrow-bore columns, as emphasized elsewhere, it is necessary to pack uniformly along the full length of the column; it is also necessary to avoid packing the column too tightly at any particular position along the column since such tight packing could unduly restrict the flow of mobile solvent through the column during operation. In addition, it is also desired to obtain uniform density of packing across the diameter of the column so as to produce high efficiency separation. The characteristics of the particular columns packed in accordance with the process of the present invention are that (a) long, narrow bore columns are efficiently packed with particles as small as 3 μm and that (b) they have a low enough porosity to permit efficient separation but yet that (c) due to the uniform and stable distribution of particles, the columns may be operated with a high flow rate (0.1–20 μl/min.).

In the preferred embodiment of the process of the present invention, a column of I.D. less than 500 μm is selected from fused silica, glass, stainless steel or glass-lined stainless steel materials. The column is connected to a slurry reservoir fixture of the type shown in FIG. 1. Narrow-bore column 10 composed of fused silica capillary tubing 11 is inserted into stainless steel tube 13. One end of tube 13 nests in union 12 and the other end nests in union 16 and is held in place by ferrule 15. Slurry reservoir 17 is also inserted into union 16; slurry reservoir 17 communicates with a pump (not shown) through union 20. The end of column 10 is thus inserted through tube 13 into an abutting relationship with the bottom of slurry reservoir 17. The lower portion of wall 19 of reservoir 17 is shaped to fit flush with internal wall 14 of union 16. In the preferred embodiment, shown in FIG. 1, the interior wall of union 16 is funnel-shaped at the center so the lower portion of wall 19 is similarly funnel shaped. At its terminus, wall 19 meets the upper end of tube 13. The upper end of capillary tubing 11 therefore only communicates with slurry 18 so that during packing the slurry flows smoothly into the end of column 10. As shown, the bottom of the funnel preferably has a diameter comparable to the I.D. of column 10 so that impedance to flow due to the door effect is avoided; during packing the slurry flows uniformly into the end of column 10.

During the packing process a particle restrictor is connected to the downstream end of the column. As discussed subsequently and as shown in the photographs of FIGS. 4a–4e, the restrictor permits a uniformly low porosity packing to be obtained. In contrast with the Ishii approach, described above, the flow of particles in the slurry under high pressure is stopped at the end of the column and the particles are collected and uniformly packed in the bed. During the packing process, the restrictor provides a back pressure and permits solvent to flow out the end of the column but retains the packing materials in the column. Typically, the packing materials have a diameter in the range of 3 to 10 $\mu m$ for LC and 3 to 100 $\mu m$ for GC.

The restrictors may take several shapes. As shown in FIG. 2a a wire 28 is inserted up the end of column 25 which has along its length an external protective coating 26. Wire insert 28 is of a diameter which is slightly less than the inner diameter of column 25 thereby allowing solvent to flow out of the column via the annular opening 29. The dimension of the annular opening 29 is small enough so that the column packing particles 27 will not pass through. Once the column is fully packed in accordance with the process of the present invention, the wire may be withdrawn and a porous plug inserted. The requirement for the plug is that mobile solvent must flow through it yet it must permanently restrict the particles to the body of the column. A second type of flow restrictor is shown in FIG. 2b. A thick walled fused silica column 30 having a small central core 32 and whose outer diameter is approximately equal to the inner diameter of column 25 is inserted in and adhered to the end of column 25. Solvent flows through the central core 32 of column 30 yet the packing particles 27 are constrained from passing out of column 31 due to the narrowness of central opening 32. A third type of restrictor is shown in FIG. 2c. Column 25 is inserted into connector tubing 33, e.g., Teflon ® tubing, whose inner diameter is approximately the size of the outer diameter of column 25. A plug insert 31 is forced against the end of column 25. Column or tubing 34 is connected to the insert 31 for detector interfacing. The opening through plug insert 31 is sufficiently narrow to prevent the particles 27 from passing through. In addition to the plug insert 31 of FIG. 2c, the insert may be a wire 39 in a column 37 as shown in FIG. 2d. Another type of restrictor is shown in FIG. 2e. This is a variation which can be applied to any of the configurations above. Here, larger size particles 35 are first packed inside the end of the column or at the interface with the end restrictor 31 (or any one of the above restrictor arragements). The larger particles are selected to be large enough so as to not pass through the opening whether it is an annular opening (FIGS. 2a, 2d), the I.D. of a column (FIG. 2b) or the central opening of a plug insert (FIG. 2c). The smaller particles that constitute the working portion of the column then are flowed through the column in accordance with the process of the invention and fill up the length of the column. The smaller particles are effectively stopped by the layer of larger particles. The restrictor used in the packing process for long length columns can also be a short packed column (e.g., 4 cm × 2 mm, 10 $\mu m$ particle packed column). After packing is completed the restrictor packed column may be removed and a permanent restrictor end fitting put in place.

The slurry reservoir is preferably filled with a high concentration (on the order of $\geq 20\%$ particles/volume) of packing material in a solvent such as methanol or acetone. The upper end of the reservoir is connected by a conventional union 20 to a high pressure pump for supplying the solvent under pressure as a mobile phase during packing. The orientation of reservoir 17 and column 10 may be as shown in FIG. 1; this results in downward packing. Preferably column 10 is located above reservoir 17 in an upward packing mode so that the microparticles do not settle in the reservoir and pack nonuniformly. To ensure uniform packing the slurry in the reservoir is preferably agitated, preferably by noncontact means such as ultrasonic means (not shown). The slurry is then pressurized in the reservoir to an initial packing pressure. The initial reservoir pressure is proportional to (a) the column length, (b) the column inner diameter, and (c) particle size. The pressure is selected in accordance with Table II for columns having an initial length of 50 cm or longer.

TABLE II

| Column Length (cm) | Column ID (mm) | Initial Pressure (atm) |
| --- | --- | --- |
| 50 | 0.5 | 50 |
| 50 | 0.3 | 150 |
| 50 | 0.2 | 300 |
| 50 | 0.1 | 400 |
| 200 | 0.5 | 200 |
| 200 | 0.3 | 300 |
| 200 | 0.2 | 400 |
| 200 | 0.1 | 500 |

As the initial pressure is attained the slurry begins to flow through the column. The reservoir pressure and flow are maintained at the initial pressure for not more than 10 minutes. Then the pressure is raised in stepwise or linear fashion from the initial pressure, in the range of 50 to 500 atmospheres, up to a pressure of 200 to 800 atmospheres. During the period the initial pressure is maintained, during the period of pressure ramping, and during the period of operation at maximum pressure mobile phase solvent is flowing and particles are being swept into and packed in the column. At the beginning of the period the initial pressure is maintained, the flow rate approaches 1 cc/minute. As the column fills up with packing material the flow rate gradually diminishes. The two-step pressure sequence (initial, then maximum) allows the bed to form uniformly and then to be compressed more tightly until the level of compression associated with the maximum pressure is asymptotically approached. The two-step sequence permits uniformity to be obtained since the bed is formed at non-turbulent lower pressures and then full compression is achieved once the particles are in place. If the maximum pressure were used initially, then non-uniformities along the length of the column could result. After operation at the maximum pressure for ten to thirty minutes the pump is then turned off and the pressure is reduced gradually through the column either stepwise or linearly. Since the reduction in pressure is gradual there is no significant backwards force to dislodge the packing material. Column 10 is then removed from tube 13 and thereby is disengaged from slurry reservoir 17. The packed bed is then purged with a chromatographic solvent in order to ready the column to be useful for chromatographic analysis.

For packing columns somewhat more densely shorter column lengths and higher initial pressures may be used. The limit on higher initial pressures is created by the non-uniformity that would be introduced if there were initial turbulent flow. The process of the present invention is practiced in the same manner except that the initial starting pressure is selected in accordance with Table III.

TABLE III

| Column Length (cm) | Column ID (mm) | Initial Pressure (atm) |
|---|---|---|
| 25 | 0.5 | 300 |
| 25 | 0.3 | 400 |
| 25 | 0.2 | 500 |
| 25 | 0.1 | 600 |
| 50 | 0.5 | 400 |
| 50 | 0.3 | 500 |
| 50 | 0.2 | 700 |
| 50 | 0.1 | 800 |

Only short columns can be packed with such higher initial pressures since columns packed at such high initial pressures would be more dense and the flow of mobile solvent would be impeded at the last incremental lengths of the column.

Columns packed by the process of the present invention in accordance with Table II have low flow resistance. Flow resistance factors are obtained in the range of 50 to 400 as defined by $\phi$:

$$\phi = \frac{d_p^2 \Delta p}{uL\eta}$$

Here
 $d_p$ = particle size,
 $\Delta p$ = pressure gradient across the column,
 $\mu$ = linear mobile solvent flow rate,
 $\eta$ = viscosity of the mobile solvent, and
 $L$ = column length.

Figure 4B:
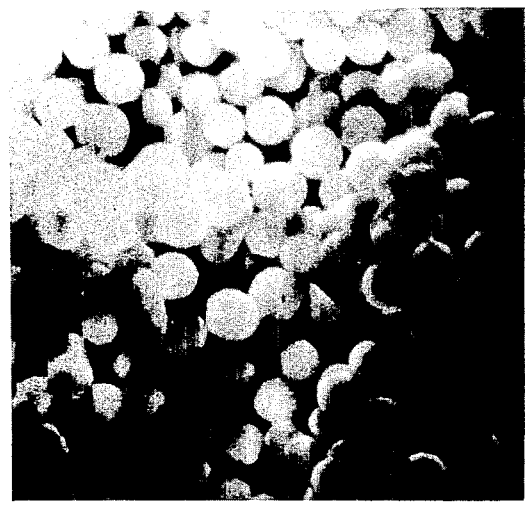
FIG. 4b is a reproduction of a photograph of a partial column cross section at the inlet end of the column near the center of the column.
Figure 4A:
FIG. 4a is a reproduction of a photograph of an entire column cross section.
Figure 4D:
FIGS. 4d-4e are reproductions of photographs of partial column cross sections at the outlet end of the column near the wall.
Figure 4C:
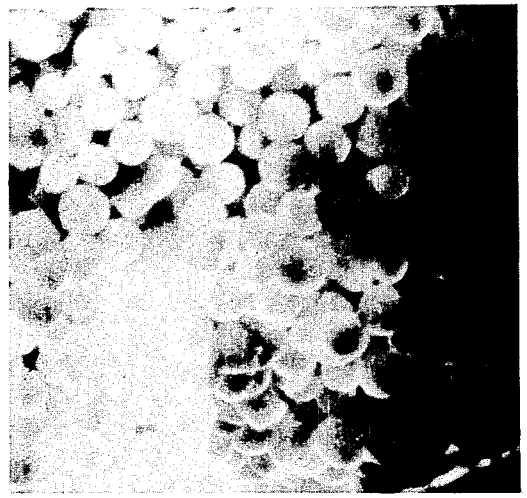
FIG. 4c is a reproduction of a photograph of a partial column cross section at the inlet end of the column near the wall.
Figure 4E:
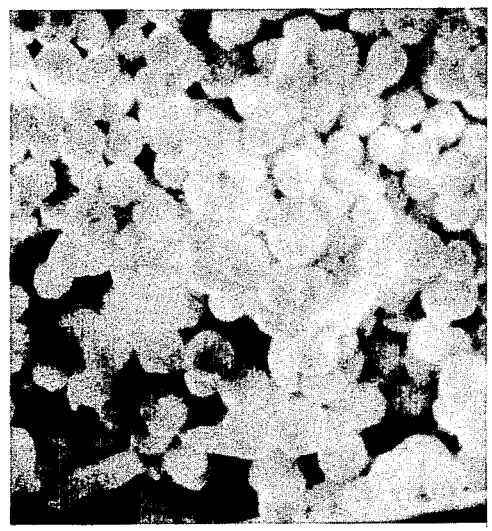

The product has a porosity $\geq 0.5$ and is classified as a loose packed column. For LC columns small particles, e.g., 3 to 10 $\mu$m, are the preferred packing materials; for GC columns particles in the range of 3 to 100 $\mu$m are preferred. The products have a substantially uniform porosity along the length and across the diameter of the column, as shown in FIGS. 4a–d. FIGS. 4b and 4c show the scanning electron-microscope (SEM) views of particle distributions at the inlet end of a 1m×0.3 mm ID 3 $\mu$m particle packed column. The Figures show that the particle distributions at the center and near the wall of the column cross section have no significant differences. The uniform distribution of particles across the column diameter is evident. FIGS. 4d and 4e show the scanning electron microscope views of particle distribution at the outlet end of the column. The SEM views show that particle size and density of distribution across the column diameter at the column end are the same. And the density and uniformity of the particle distribution as shown in FIGS. 4a–b and 4c–d are the same. This indicates the uniformity of packing along the length of the column. This uniformity is corroborated by the full cross sectional view of FIG. 4a. This uniformity is contrasted with columns packed by conventional techniques in which larger particles tend to collect along the walls as the walls exert higher drag forces on the larger particles. This uniformity is advantageous because no extraband spreading effects occur when samples are analyzed and thus the columns are highly efficient. For column lengths greater than or equal to 50 cm such loose packed columns are preferred since they permit mobile solvent to flow at reasonable flow rates on the order of 0.1 to 20 microliters/min during the performance of chromatographic analysis. Even though the porosity is high, the packing materials are found not to settle with use. This is due to the fact that even though the columns are operated at high pressure the total force being applied to the packed bed is small, since the crosssectional area is small. Such columns permit a fast analysis to be accomplished because at high pressures high flow rates can be attained. Because long length columns can be packed with 3 $\mu$m or smaller particles for LC, very high resolution power can be obtained.

The specification of columns packed in accordance with the process of the present invention including their performance is reported in detail in F. J. Yang, "Fused-Silica Narrow-Bore Microparticle-Packed-Column High-Performance Liquid Chromatography", *J. Chromatography*, v. 235, p. 265 (1982) at p. 266. Some of the notable comparisons between prior art columns and these columns are given in Table IV:

TABLE IV

| Feature | Prior Art | Present Invention |
|---|---|---|
| Column Plate Number | 20,000–30,000 (4.6 mm, ID, 25 cm) | 200,000 (300 $\mu$m ID, 2 meters) |
| Peak Capacity | 50 | 150–200 |
| Solvent Utilization | 1 cc/min. | 2 $\mu$l/min. |
| Sample Size | 1 mg. | 10 micrograms |

Figure 5:
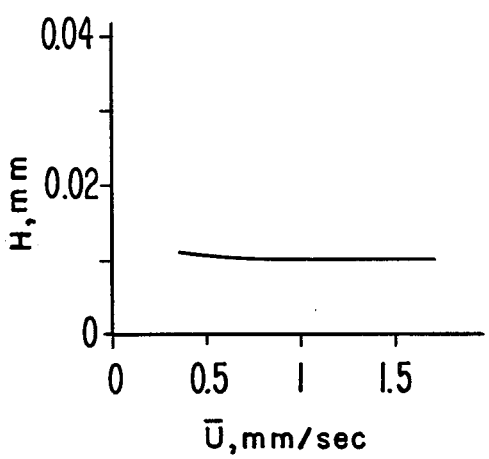
FIG. 5 is a Van Deemter performance plot for a 3 μm $C_{18}$ Bonded-phase particle 330 μm I.D. narrow bore microparticle packed column where the test compound was pyrene.

Fused-silica tubing with I.D. ranging from 57 to 376 $\mu$m and with lengths up to 2 m was packed with 3, 5 and 10 $\mu$m C$_{18}$ bonded-phase particles using the packing technique of the present invention. Reversed-phase octadecylsiloxane was chemically bonded onto the microparticulate silica before packing into the microbore columns. The mobile phase was 70:30 acetonitrile-water under isocratic conditions. The resolving power of the column is indicated by the Van Deemter plot of FIG. 5 for 1 m×330 $\mu$m I.D. columns packed with spherical 3 $\mu$m C$_{18}$ bonded silica particles. It shows no significant flow rate effect. For the flow rates range between 0.3 and 1.6 mm/sec, column efficiency maintains at its high value due to the uniformity of the packed bed of the column. The total column plate number exceeded 110,000 for the flow-rate range studied. This compares with column plate numbers of 20,000 for conventional columns.

Figure 6:
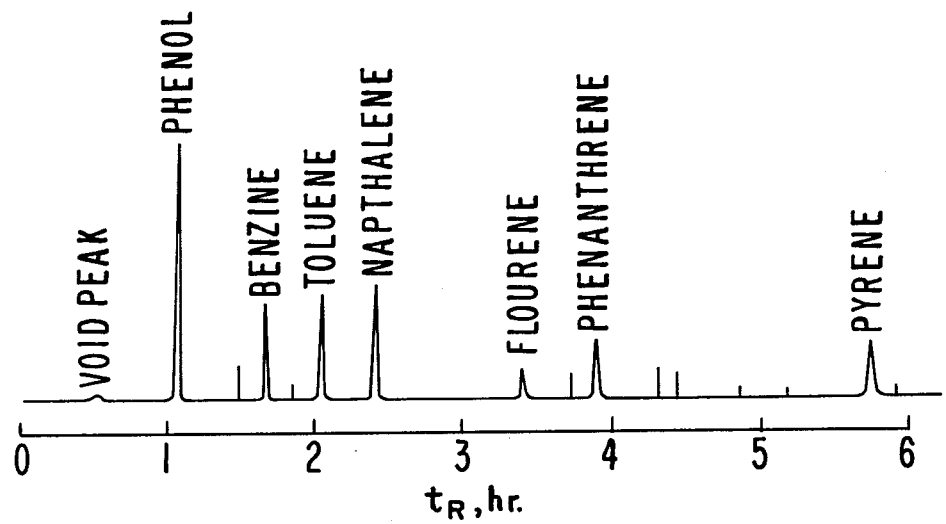
FIG. 6 is a chromatogram showing the separation of a mixture of polynuclear aromatic hydrocarbons.
Figure 7:
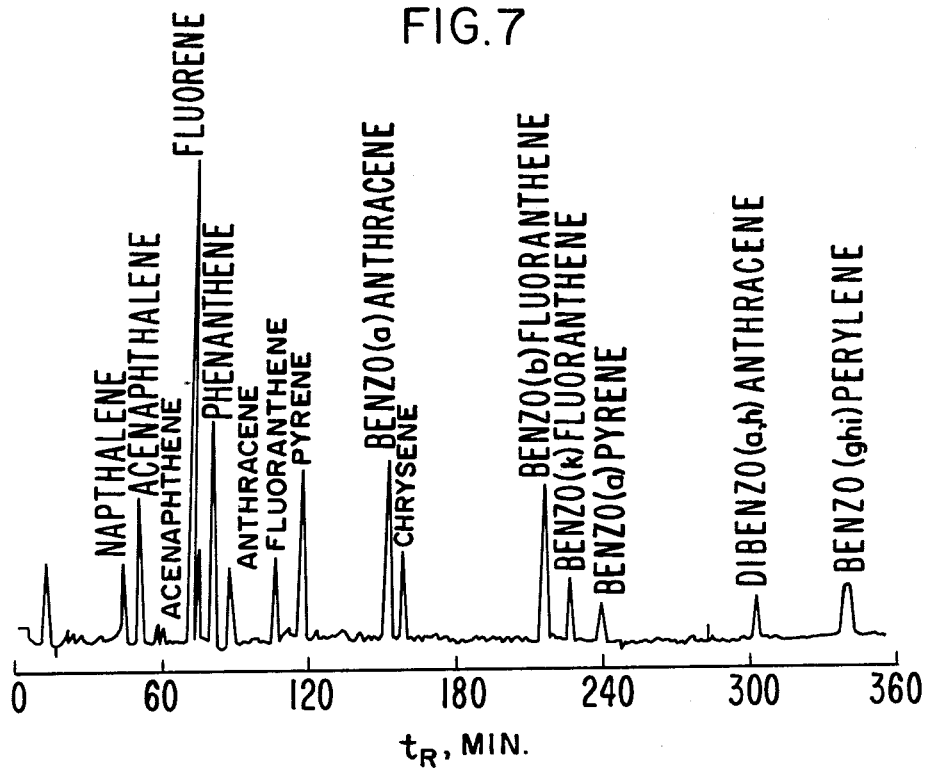
FIG. 7 is a chromatogram showing separation of an EPA priority pollutant PNA sample using a 320 μm × 1 m, 3 μm $C_{18}$ reverse phase column.

The resolving power of the product of the process of the present invention is further shown by the chromatograms of FIGS. 6 and 7. FIG. 6 shows the separation of a mixture of polynuclear aromatic hydrocarbons by a 320 μm×2 meter fused silica column packed by the process of the present invention with 3 μm $C_{18}$ bonded reverse phase silica particles. The mobile solvent was 70% acetonitrile: $H_2O$ and the flow rate was 1.8 μl/minute. For the two meter column, the total column plate number measured for pyrene with $k'=10$ was 144,000 plates. The total single column efficiency of 144,000 plates has not previously been reported for 3 μm $C_{18}$ column. It demonstrates the effectiveness of the packing technique for packing long column with small particles. In FIG. 7 an EPA priority pollutant PNA sample was separated using a 320 m×1 meter fused silica column packed by the process of the present invention with 3 μm reverse phase bonded silica particles. The mobile solvent was 70% acetonitrile: $H_2O$ and the flow rate was 0.9 μl/minute. Note that baseline resolution of the PNA mixture was obtained. In particular, note the separation of benzo(a)anthracene and chrysene which is normally concealed in isocratic reverse phase system. The advantages of using long narrow-bore microparticle packed column in complex sample analysis and in solvent saving are evident.

The selection of column materials for narrowbore microparticle packed liquid and gas chromatography may be made from the following materials: fused silica, glass, stainless steel and glass-lined stainless steel. The requirement is that the material be inert and capable of being formed in the requisite narrow diameters. Preferably, the materials, when formed with narrow diameters, are flexible so that long lengths can be coiled to occupy small volumes. In addition, the materials have preferably smooth inner surfaces and do not exhibit wall effects. It has been found that fused silica is a preferred material due to the extreme smoothness of its inner walls and to its ability to dissipate heat through the walls; with such heat dissipation there is no significant temperature gradient across the column. Fused silica columns also are ideal for interfacing directly to detectors such as flame base detectors, mass spectrographs and Fourier Transform Infrared Detectors, since the flow rates are matched to the flow requirements of these detectors. Columns packed in accordance with the process of the present invention typically will have an inner diameter less than about 500 μm. For liquid chromatography they have a particle size of less than 10 μm and a length of more than 10 cm. For gas chromatography they have a particle size of less than 100 μm. The particles may be physically coated or have bonded to them any types of phases useful for gas, liquid, gel or ion-exchange chromatography.

What is claimed is:

1. A process for slurry packing a narrow bore column with inner diameter less than 0.5 mm, comprising the steps of:
   selecting a column having an inner diameter less than 0.5 mm, said column having an exit end;
   preparing a slurry from a mobile solvent and a packing material;
   plugging said exit end with an end restrictor which permits said mobile solvent to flow therethrough, but which restricts the passage of said packing material;
   causing said slurry to flow through said column under pressure in the following manner:
   applying an initial pressure and maintaining said initial pressure for an initial period until said column is filled up to form a bed;
   raising the pressure from said initial pressure to a maximum pressure; and
   maintaining said maximum pressure for a second period.

2. A process for slurry packing a narrow bore column specifically for gas chromatography in accordance with claim 1 wherein said step of preparing a slurry from a mobile solvent and a packing material is accomplished by the step of preparing a slurry from a mobile solvent and a packing material composed of particles having a diameter in the range of 3 μm to 100 μm.

3. A process for slurry packing a narrow bore column specifically for liquid chromatography in accordance with claim 1 wherein said step of preparing a slurry from a mobile solvent and a packing material is accomplished by the step of preparing a slurry from a mobile solvent and a packing material composed of particles having a diameter in the range of 3 μm to 10 μm.

4. A process for slurry packing a narrow bore column in accordance with claims 2 or 3 wherein said step of applying an initial pressure and maintaining said initial pressure for an initial period is accomplished by the step of applying an initial pressure selected from the following Table and maintaining said initial pressure for an initial period of less than 10 minutes:

| Column Length (cm) | Column ID (mm) | Initial Pressure (atm) |
| --- | --- | --- |
| 50 | 0.5 | 50 |
| 50 | 0.3 | 150 |
| 50 | 0.2 | 300 |
| 50 | 0.1 | 400 |
| 200 | 0.5 | 200 |
| 200 | 0.3 | 300 |
| 200 | 0.2 | 400 |
| 200 | 0.1 | 500 |

5. A process for slurry packing a narrow bore column in accordance with claim 4 wherein said step of maintaining said maximum pressure is accomplished by the step of maintaining said maximum pressure for a period of more than ten minutes.

6. A process for slurry packing a narrow bore column in accordance with claim 4 wherein after the step of preparing a slurry and before the step of causing said slurry flow through said column under pressure, the following step is added:
   agitating said slurry.

7. A process for slurry packing a narrow bore column in accordance with claim 6 wherein said step of agitating said slurry is accomplished by the step of ultrasonically agitating said slurry.

8. A process for slurry packing a narrow bore column in accordance with claim 1 wherein said step of plugging the exit end of said column is accomplished by the step of plugging the exit end of said column with a narrow bore tubing which permits the flow of mobile solvent but which restricts the passage of said packing material.

9. A process for slurry packing a narrow bore column in accordance with claim 1 wherein said step of plugging the exit end of said column is accomplished by the step of plugging the exit end of said column with a wire such that an annular passage is formed between the wire and the column to allow the flow of mobile solvent and to restrict the passage of said packing material.

10. A process for slurry packing a narrow bore column in accordance with claim 1 wherein said step of plugging the exit end of said column is accomplished by the steps of
applying a sleeve over the end of said column; and
inserting a narrow bore plug into said sleeve which abuts the end of said column.

11. A process for slurry packing a narrow bore column in accordance with claim 1 wherein said step of plugging the exit end of said column is accomplished by the steps of:
applying a sleeve over the end of said column;
inserting an extension column into said sleeve into abutting relationship with the end of said column; and
inserting a needle into the end of said extension column.

12. A process for slurry packing a narrow bore column in accordance with any of claims 8–11 including before the step of flowing said slurry under pressure through said column and after the step of plugging the end of said column, the step of placing at the end of said column adjacent said end restrictor a collection of particles of diameter larger than the constituent particles of said packing material to form thereby a stop layer for said packing material.

13. A process for slurry packing a narrow bore column in accordance with claim 1 wherein said step of selecting a column is accomplished by the step of selecting a flexible column from the materials fused silica, stainless steel or glass-lined stainless steel.

14. A process for slurry packing a narrow bore column in accordance with claim 13 wherein said step of selecting a column comprises the step of selecting a flexible column of fused silica of length greater than 50 cm.

15. A process for slurry packing a narrow bore column in accordance with claim 4 wherein after said step of maintaining said maximum pressure for a second period the following step is added:
gradually reducing the pressure of said slurry in said column.

16. A process for slurry packing a narrow bore in accordance with claim 1 wherein said column is flexible.

17. A narrow bore packed column with inner diameter less than 0.5 mm produced in accordance with the following process:
selecting a flexible column having an inner diameter less than 0.5 mm, said flexible column having an exit end;
preparing a slurry from a mobile solvent and a packing material;
plugging said exit end with an end restrictor which permits said mobile solvent to flow therethrough, but which restricts the passage of said packing material;
causing said slurry to flow through said column under pressure in the following manner:
applying an initial pressure and maintaining said initial pressure for an initial period until said column is filled up;
raising the pressure from said initial pressure to a maximum pressure; and
maintaining said maximum pressure for a second period.

* * * * *